June 29, 1965 H. C. SWIM ETAL Plant Pat. 2,542
ROSE PLANT
Filed March 31, 1964
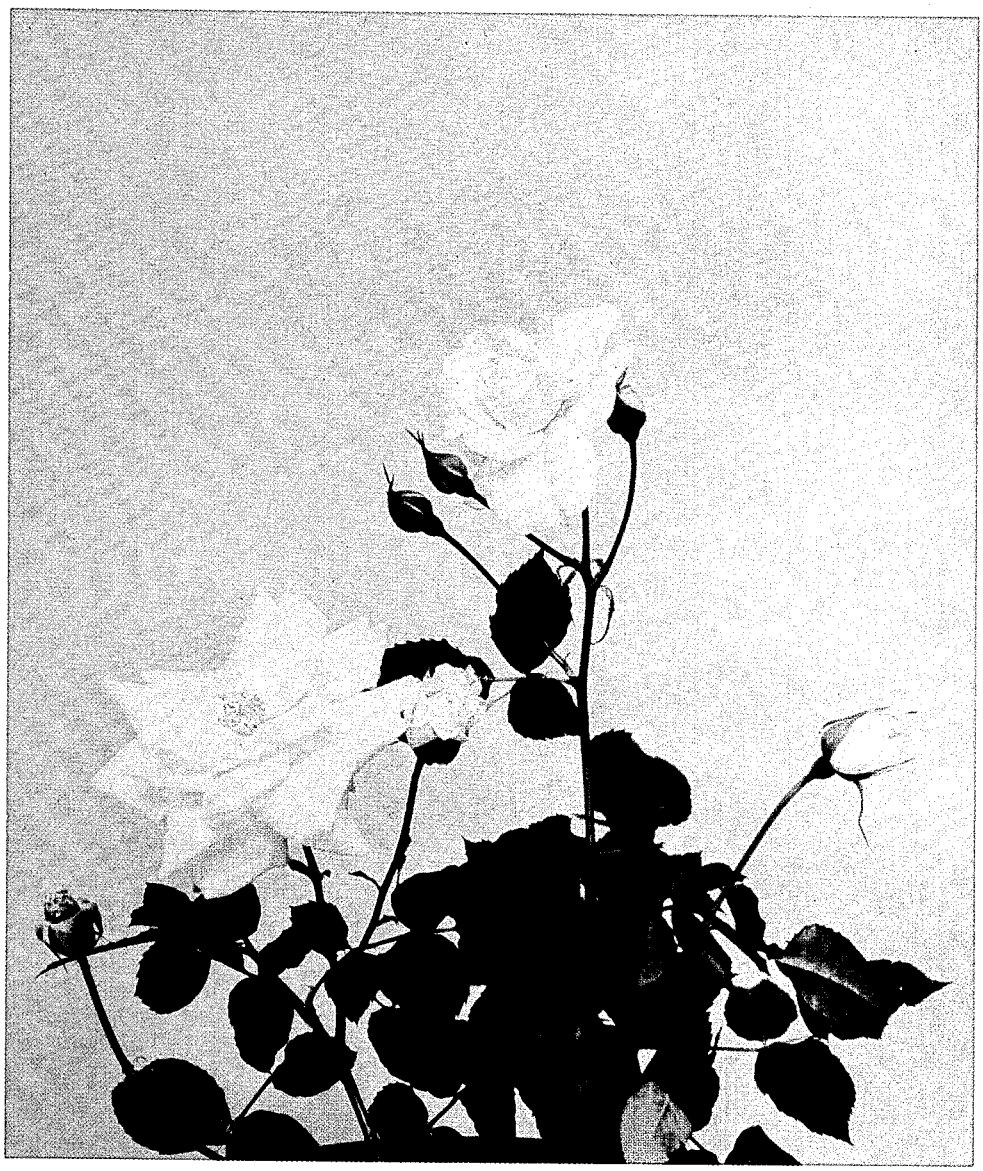
Inventors.
H. C. Swim and
O. L. Weeks
By: Robb & Robb
Attorneys.

United States Patent Office

Plant Pat. 2,542
Patented June 29, 1965

2,542
ROSE PLANT

Herbert C. Swim, Ontario, and O. L. Weeks, Chino, Calif., assignors to O. L. Weeks, doing business under the trade name and style of Weeks Wholesale Rose Grower, Chino, Calif.

Filed Mar. 31, 1964, Ser. No. 356,343
1 Claim. (Cl. Plt.—24)

The present invention relates to a new and distinct variety of rose plant of the floribunda class, which was originated by us by crossing the variety "Frolic" (Plant Patent No. 1,179) with the variety "Lavender Pinocchio" (Plant Patent No. 947).

As the result of this breeding, we have produced a new rose variety having the following unique combination of characteristics which are outstanding therein and which distinguish it from its parents, as well as from all other varieties of which we are aware:

(1) A low-growing, compact but somewhat spreading habit of plant growth;

(2) A distinctive and attractive form and good petalage of the buds and flowers;

(3) An intermittent habit of bloom, with relatively few flowers bridging the gap between peak blooms;

(4) A massive color effect of the plants when in full bloom;

(5) A distinctive and attractive lemon and white general color tonality of the flowers; and (6) A variable flower fragrance ranging from tea rose to that of the common lilac (*Syringa vulgaris*).

In comparison with its seed parent "Frolic," the plants of our new variety are substantially lower growing and more spreading in habit; the flowers are larger, ranging from 3 inches to 3½ inches in diameter, as compared with 2½ inches in the case of fully opened flowers of this parent variety; the flowers have greater petalage, ranging from 28 to 55 petals, as compared with the range of 18 to 23 petals in the flowers of "Frolic"; and the flower color is best described as ranging from lemon to white, whereas the flowers of "Frolic" are bright pink.

As compared with the pollen parent "Lavender Pinocchio," the plant of our new variety is substantially lower growing; the new variety gives the effect of a more solid mass at the bloom peak than is the case of this parent variety; the flowers have greater petalage in comparison with the petalage of this parent variety which ranges from 25 to 30 petals; and the flowers have a completely different color, ranging from lemon to white, whereas those of "Lavender Pinocchio" range from light chocolate-olive-brown in the bud stage, and pink lavender in the open flower stage.

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Dwarf; bush; outdoor; seedling for garden decoration.

Class: Floribunda.

Breeding: Seedling.

*Seed parent.*—"Frolic."

*Pollen parent.*—"Lavender Pinocchio."

Propagation: Holds its distinguishing characteristics through succeeding propagations by budding.

*Flower*

Locality where grown and observed: Chino, California.

Flowers borne: From singly to several to stem; in irregular to regular cluster; on weak to normal strength, short stems.

Quantity of bloom: Abundant, both outdoors and in greenhouse.

Continuity: Intermittent.

Fragrance: From slight to moderate; variable. Nature—from tea rose to lilac (*Syringa vulgaris*).

Bud:

*Peduncle.*—Short length (4–5 cm.); slender caliper; bending very slightly; smooth, except for numerous stipitate glands. Color—yellowish green.

*Before calyx breaks.*—Size—from medium to small for class. Form—medium length; pointed; with a conspicuous neck; rarely with foliaceous appendages on the surface of the bud; with slender sepal points extending beyond the tip of the bud equal to ¼ to ½ of its length. Color—near Brilliant Yellow Green, Plate 2.5GY 9/8 between sepals.

*As calyx breaks.*—Color—Brilliant Greenish-Yellow, Plate 10Y 9/9.

*As petal first opens.*—Size—from medium to large for class. Form—ovoid. Color: outside—ranging from Brilliant Greenish-Yellow, Plate 7.5Y 9/8 over upper portion to Brilliant Greenish-Yellow, Plate 10Y 9/9 over lower portion and along midrib in its entirety; Inside—near Brilliant Yellow, Plate 5Y 9/9 over most of petal but near Vivid Yellow, Plate 5Y 8/12 over lower ⅓ reaching greatest intensity at point of attachment.

*Opening.*—Ordinarily opens up well, but is retarded from opening by cold, wet weather.

Bloom:

*Size (when fully open).*—From medium to large for class; from 3 inches to 3½ inches.

*Petalage.*—Double; from 28 to 55 petals; arranged regularly; 3 to 6 petaloids at center; usually with stamens showing.

*Form.*—High-centered at first, but becoming flat to open at maturity; petals being at first loosely rolled outward, but becoming slightly more tightly rolled outward at maturity.

Petals:

*Texture.*—Moderately thin; moderately soft.

*Appearance.*—Inside—velvety. Outside—shiny to satiny.

*Shape.*—Outside—nearly round, with one notch usually on both sides of sharp-pointed apex. Intermediate—elliptical, with apex acute. Inside—obobate-cuneate, with apex acute or sometimes unpointed.

This description of a newly opened flower was made from a rose grown in a greenhouse during the month of February at Chino, California:

*Color.*—Outer petal: outside surface—ranging from Brilliant Greenish-Yellow, Plate 7.5Y 9/8 over upper portion to Brilliant Greenish-Yellow, Plate 10Y 9/9 over lower portion and along midrib in its entirety; inside surface—near Brilliant Yellow, Plate 5Y 9/9 over most of petal, but near Vivid Yellow, Plate 5Y 8/12 over lower ⅓, reaching greatest intensity at point of attachment. Intermediate petal: outside surface—near Brilliant Greenish-Yellow, Plate 7.5Y 9/8 over nearly entire petal, but slightly faded on upper portion and somewhat more intense over lower portion; near Vivid Yellow, Plate 5Y 8/12 at point of attachment; inside surface—between Brilliant Yellow, Plate 2.5Y 9/9, and white over upper ⅓ and nearly Brilliant Yellow, Plate 5Y 9/9 over remainder, except close to Vivid Yellow, Plate 5Y 8/12 at point of attachment. Inner petal: outside surface—between Brilliant Yellow, Plate 5Y 9/9 and white, gradually intensifying progressively toward base to Brilliant Yellow, Plate 5Y 9/9; insure surface—between Brilliant Yellow, Plate 5Y 9/9 and white, gradually intensifying progressively toward base to Brilliant Yellow, Plate 5Y 9/9.

This description was made from a rose that was open for three days in a greenhouse during the month of February at Chino, California:

*Color.*—Outer petal: outside surface—near white, with very faint yellow tint, the latter somewhat more noticeable at base; inside surface—near white, with very faint yellow tint, the latter color being more noticeable at base. Inner petal: outside surface—near white with faint creamy tint somewhat more noticeable at base; inside surface—very near white, but with a faint yellowish tint in area at base.

*General color effect.*—Newly opened flower—center near Brilliant Yellow, Plate 5Y 9/9, with outer edges of flower between Brilliant Yellow, Plate 5Y 9/9 and white. Three-days open—near white, with slight creamy or yellowish tint in the center area.

*Behavior.*—Normally drop off cleanly, but affected by extremes of cold, hot, wet and dry weather, resulting in some petals hanging on or at other times a few petaloids persisting.

*Flower longevity.*—Cut roses grown in greenhouse and kept at living room temperatures—3 days in February.

*Reproductive organs*

Stamens: Medium quantity; arranged more or less regularly about pistils; sometimes mixed with petaloids.
Filaments: Short; most with anthers. Color—yellow.
Anthers: Large for class all open at once. Color—yellow.
Pollen: From moderate to abundant. Color—yellow.
Pistils: From few to medium in quantity.
Styles: Somewhat uneven; short; medium thin caliper; loosely bunched.
Stigma: Color—yellow.
Ovaries: Usually all enclosed in calyx.
Hips: Globular very smooth. Color—yellow when mature.
Sepals: Permanent; moderately short; curled.
Seeds: Few; from small to medium for class.

*Plant*

Foliage:

*Leaves.*—Compound of 3–7 leaflets moderately abundant; moderately large; moderately thin; somewhat soft.

*Leaflets.*—Shape—ovoid, with apex variably acute or acuminate. Base—from rounded to acute. Margin—simply serrate.

*Color.*—Mature: upper surface—from light to medium yellowish green; under surface—light grey-green. Young: upper surface—from light to medium yellowish-green, with bronze serrations and reticulations; under surface—from light to medium yellowish-green, with bronze serrations and reticulations; influence of bronze from reticulations gives effect of slight bronze overlay.

*Rachis (the supporting stem of the compound leaf).*—From light to medium weight. Upper side—grooved; stipitate gland on ridges occasionally. Under side—smooth.

*Stipules.*—From short to medium length; narrow; with short points turning out at an angle of about 45°.

*Disease resistance.*—When compared to other varieties grown under similar cultural and climatic conditions, this variety shows medium resistance to powdery mildew and substantially better than average resistance to rose rust.

Growth:

*Habit.*—Dwarf; bushy; spreading but compact; much-branched.

*Growth.*—Free.

*Canes.*—Moderately light.

*Main stems.*—Color—dull grey-green. Large prickles—several; medium length; straight; with short, broad base; color—brown. Small prickles—few; color—brown. Hairs—none.

*Branches.*—Color—dull grey-green. Large prickles—several; medium length; straight; with short, broad base; color—brown. Small prickles—few; color—brown. Hairs—none.

*New shoots.*—Bright yellowish-green. Large prickles—several; medium length; straight; with short, narrow base; color—reddish, with green tips. Small prickles—few; color—reddish. Hairs—none.

We claim:

A new and distinct variety of rose plant of the floribunda class, substantially as herein shown and described, characterized particularly as to novelty by the unique combination of a low-growing, compact but somewhat spreading habit of plant growth, distinctive and attractive form and good petalage of the buds and flowers, an intermittent habit of bloom, with relatively few flowers bridging the gap between peak blooms, a massive color effect of the plants when in full bloom, a distinctive and attractive lemon and white general color tonality of the flowers, and a variable flower fragrance ranging from tea rose to that of the common lilac (*Syringa vulgaris*).

No references cited.

ABRAHAM G. STONE, *Primary Examiner.*